United States Patent
Wulf

(10) Patent No.: US 10,271,723 B2
(45) Date of Patent: Apr. 30, 2019

(54) METHOD AND APPARATUS FOR PROVIDING A REFERENCE LEVEL FOR AN EYE-OPENING WIDTH

(71) Applicant: Robert Bosch GmbH, Stuttgart (DE)

(72) Inventor: Felix Wulf, Ludwigsburg (DE)

(73) Assignee: ROBERT BOSCH GMBH, Stuttgart (DE)

( * ) Notice: Subject to any disclaimer, the term of this patent is extended or adjusted under 35 U.S.C. 154(b) by 30 days.

(21) Appl. No.: 15/187,933

(22) Filed: Jun. 21, 2016

(65) Prior Publication Data

US 2016/0367127 A1    Dec. 22, 2016

(30) Foreign Application Priority Data

Jun. 22, 2015 (DE) ......................... 10 2015 211 443

(51) Int. Cl.
| | |
|---|---|
| *A61B 3/00* | (2006.01) |
| *A61B 5/18* | (2006.01) |
| *A61B 3/10* | (2006.01) |
| *A61B 5/11* | (2006.01) |
| *A61B 5/16* | (2006.01) |

(52) U.S. Cl.
CPC .......... *A61B 3/0025* (2013.01); *A61B 3/1005* (2013.01); *A61B 5/1103* (2013.01); *A61B 5/1128* (2013.01); *A61B 5/165* (2013.01); *A61B 5/18* (2013.01); *A61B 2503/20* (2013.01)

(58) Field of Classification Search
CPC ........ A61B 3/0025; A61B 3/1005; A61B 5/18
USPC ................................ 351/205, 206, 209, 246
See application file for complete search history.

(56) References Cited

FOREIGN PATENT DOCUMENTS

WO    WO2014031042 A1    2/2014

*Primary Examiner* — Jack Dinh
(74) *Attorney, Agent, or Firm* — Norton Rose Fulbright US LLP; Gerard Messina

(57) ABSTRACT

A method for providing a reference level for an eye-opening width, the eye-opening width representing an instantaneously detected distance between the eyelids of an eye, the method having an ascertainment step, in which the reference level is ascertained using values of the eye-opening width, where the eye-opening width is greater than a limiting value.

15 Claims, 2 Drawing Sheets

METHOD AND APPARATUS FOR PROVIDING A REFERENCE LEVEL FOR AN EYE-OPENING WIDTH

CROSS REFERENCE

The present application claims the benefit under 35 U.S.C. § 119 of German Patent Application No. 102015211443.0 filed on Jun. 22, 2015, which is expressly incorporated herein by reference in its entirety.

FIELD

The present invention relates to an apparatus, method, and computer program for providing a reference level for an eye-opening width.

BACKGROUND INFORMATION

The drowsiness of a driver of a vehicle may be judged indirectly from his/her driving behavior.

Alternatively, PCT Application No. WO 2014031042 A1 describes fitting an eye-opening signal to predefined modeled signals in order to detect blinking events, and from that, to draw conclusions about the attentiveness of the driver.

SUMMARY

In accordance with the present invention, an example method provides a reference level for an eye-opening width. An apparatus which uses this method, and finally, a corresponding computer program are also provided.

To evaluate drowsiness of a driver, a reference value of an eye-opening width is necessary, since the eye-opening width varies in phases in which the eyes are open, e.g., on the basis of lighting conditions. In order to obtain a utilizable reference value, phases in which the eyes are closed may be excluded from a calculation of the reference value. If these phases were taken into account, the reference value would be too low.

A method is introduced for providing a reference level for an eye-opening width, the eye-opening width representing an instantaneously detected distance between the eyelids of an eye, the method having the step of ascertainment in which the reference level is ascertained using values of the eye-opening width, where the eye-opening width is greater than a limiting value.

A reference level may be understood to be an averaged value that is averaged within a definable time window from fluctuation-encumbered values. Values of the eye-opening width, where the eye-opening width is less than the limiting value may be left out of consideration.

For example, this method may be implemented in software or hardware or in a mixed form of software and hardware, e.g., in a control unit.

In addition, the reference level may be ascertained using support values. The support values may replace the values of the eye-opening width that are smaller than the limiting value. The values of the eye-opening width which are smaller than the limiting value may be discarded. Support values are able to close gaps, resulting owing to the discarded values of the eye-opening width, in a time sequence of values of the eye-opening width. Calculation of the reference level may be simplified by the support values.

The method may have a step of adaptation or alteration, in which the limiting value is tracked and/or altered using the reference level, and alternatively or additionally, using a moving average of the values of the eye-opening widths. The adaptation may be implemented as a general alteration. Tracking here may be understood to be altering of the limiting value as a function of previous values for the eye-opening width or the reference level. In this context, in particular, an increase of the values of the eye-opening width preceding in time or of the reference level may result in an increase of the limiting value. For example, the limiting value may be a percentage value of the reference level. The limiting value, as of which the values of the eye-opening width are no longer taken into account, thus lies by a fixed percentage below the reference level. A moving average may be determined over a shorter period of time than the reference level. The period of time may be longer than an anticipated blink duration.

Furthermore, in the step of adaptation or alteration, the support values which replace values of the eye-opening width that are smaller than the limiting value may be tracked or altered. Tracking here may be understood to be an alteration of the support values as a function of previous values for the eye-opening width or the reference level. In this context, in particular, an increase of the values of the eye-opening width preceding in time or of the reference level may result in an increase of the support values. The support values may likewise be tracked using the reference level and, alternatively or additionally, using a moving average of the values of the eye-opening widths.

In addition, the reference level may be ascertained using a speed limiting value. In this case, the values of the eye-opening width may be used when an eyelid speed is less than the speed limiting value. The speed limiting value thus relates to an eyelid speed. During blinking, the eyelids are moved very quickly. The blinking may be recognized in consideration of the eyelid speed, before there is a drop below the limiting value.

The reference level may be ascertained as reference characteristic. In this context, a time characteristic of the eye-opening width may be used in intervals or periods of time in which the values of the eye-opening width are greater than the limiting value. The reference level may be ascertained continuously. Consequently, an instantaneous reference level is always available.

The values of the eye-opening width may be smoothed. For instance, the values may be averaged. The values may likewise be weighted. A simplified ascertainment is thereby possible.

An apparatus is also provided, which is designed to carry out, control or put into effect the steps of a variant of a method presented here, in suitable devices. The object of the present invention may be achieved quickly and efficiently by this embodiment variant of the present invention in the form of an apparatus, as well.

In the present case, an apparatus may be understood to be an electrical unit that processes sensor signals and outputs control signals and/or data signals as a function thereof. The apparatus may have an interface which may be implemented in hardware and/or software. In the case of a hardware implementation, the interfaces may be part of what is termed a system ASIC, for example, that includes a wide variety of functions of the apparatus. However, it is also possible that the interfaces are separate, integrated circuits or are made up at least partially of discrete components. In the case of a software implementation, the interfaces may be software modules which, for example, are available in a microcontroller in addition to other software modules.

Also of advantage is a computer-program product or computer program having program code that may be stored on a machine-readable carrier or storage medium such as a semiconductor memory, a hard-disk storage or an optical memory, and is used to carry out, put into effect and/or control the steps of the method according to one of the previously described specific embodiments, especially when the program product or program is executed on a computer or a device.

Exemplary embodiments of the present invention are shown in the figures and explained in greater detail below.

DETAILED DESCRIPTION OF EXAMPLE EMBODIMENTS

Figure 1:
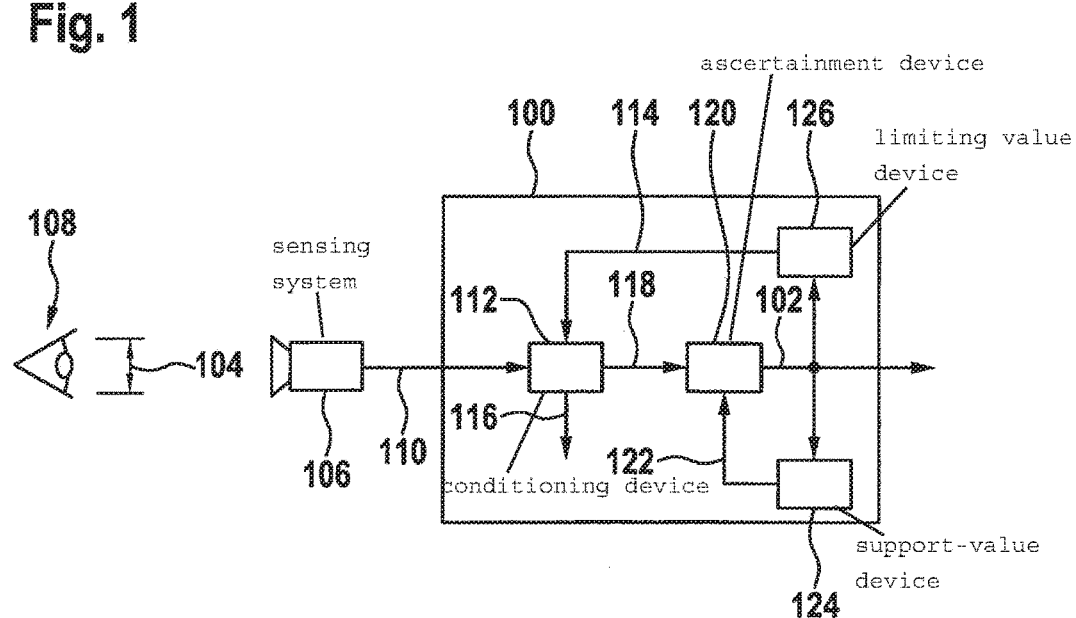
FIG. 1 shows a block diagram of an apparatus for providing a reference level for an eye-opening width according to one exemplary embodiment.

In the following description of advantageous exemplary embodiments of the present invention, the same or similar reference numerals are used for the similarly functioning elements shown in the various figures, a repeated description of these elements being omitted.

FIG. 1 shows a block diagram of an apparatus 100 for providing a reference level 102 for an eye-opening width 104 according to one exemplary embodiment. Eye-opening width 104 is sensed here at one or both eyes 108 of a driver of a vehicle by a sensing system 106 and reflected in an eye-opening-width signal 110. Eye-opening width 104 represents an instantaneous distance between the eyelids of eye 108. Eye-opening-width signal 110 is read in by apparatus 100 at an input of apparatus 100. In apparatus 100, eye-opening-width signal 110 is conditioned in a conditioning device 112. Conditioning device 112 may also be referred to as filter 112. In this context, a value of eye-opening-width 104 is compared to a limiting value 114. Signal portions 116 which represent values less than limiting value 114 are separated out and discarded. Signal portions 118 which represent values greater than limiting value 114 are passed on to an ascertainment device 120. In ascertainment device 120, reference level 102 is ascertained from the values of eye-opening width 104, where eye-opening width 104 is greater than limiting value 114. Reference level 102 is made available at an output of apparatus 100.

In one exemplary embodiment, reference level 102 is ascertained using support values 122. Support values 122 are used to fill in the gaps in eye-opening-width signal 110 resulting from the segregating of signal portions 116. Due to support values 122, reference level 102 is able to be ascertained continuously.

Support values 122 are a function of reference level 102. A support-value device 124 reads in reference level 102 and uses reference level 102 to provide support values 122.

In one exemplary embodiment not shown, support-value device 124 reads in eye-opening-width signal 110, or signal portions 118 lying above limiting value 114, directly, in order to generate support values 122.

Limiting value 114 is likewise a function of reference level 102. A limiting-value device 126 reads in reference level 102 and uses reference level 102 to provide limiting value 114.

In one exemplary embodiment not shown, limiting-value device 126 reads in eye-opening-width signal 110, or signal portions 118 lying above limiting value 114, directly, in order to generate limiting value 114.

A system 100 is introduced for the robust detection of an instantaneous eye-opening degree (EON) 104.

Based on data from a video camera 106, an instantaneous opening degree 104 of eyes 108 may be detected. Suitable image-processing algorithms are used for that purpose. In the process, in each case an eye-opening level 102 is detected for both eyes 108.

From eye-opening degrees 104 of two eyes 108, one common eye-opening level 102 is able to be calculated. Instantaneous eye-opening level 102 may be calculated using Savitzky-Golay filters.

The approach presented here permits an improvement in the detection quality of blinking features on the basis of eye-opening data 118 pre-filtered beforehand. In this context, an instantaneous eye-opening level 102 is calculated. Eye-opening level 102 may be denoted as EOL 102. Using eye-opening level 102, blinking events may be detected easily and robustly with limiting values 114 that are defined relative to eye-opening level 102. Certain features of the blinking events like, for example, the blinking amplitude may easily be calculated. A PERCLOS value, which relates to the 90th percentile of eye-opening level 102 as maximum degree of opening, is able to be calculated robustly. The calculation of eye-opening level 102 may be incorporated into an overall system for detecting sleepiness and/or momentary drowsiness.

Eye-opening level 102 indicates how great instantaneous distance 104 is between the eyelids in the open state. In the calculation of eye-opening level 102 presented here, possible blinking events are not taken into account in calculated value 102. In this way, eye-opening level 102 is uninfluenced by the blinking frequency and the blink duration. Otherwise, the greater the frequency and duration of the blinking events, the lower the resulting eye-opening level would become.

Therefore, the calculation of eye-opening level 102 breaks down into several steps. First of all, a robust and simple detection is carried out of intervals 116 with temporarily too low an eye-opening degree 104 like, for example, blinking events or glances at the speedometer. These intervals 116 may be identified in several ways.

In one exemplary embodiment, eye-opening data 110 are strongly filtered. All intervals 116 in which eye-opening degree 104 is lower than the filtered are excluded. For example, they may be filled with a substitute value 122.

For instance, this substitute value 122 may be made up of the 90th percentile of eye-opening degree 104 of the last 150 seconds.

In one exemplary embodiment, a moving median 114 is used to effectively rule out blinking events. In this case, the median filter has a window length of at least double the maximum blink duration to be excluded. In order to effectively rule out blinking events up to a duration of a maximum of one second, a window size of two seconds may be used, for example.

All intervals 116 in which the degree of eye-opening is markedly lower than a smoothed median 114, e.g., with a deviation of more than 10 %, are considered as excluded.

Blinking events are characterized in that the absolute speed of the lid exceeds a certain value like, e.g., 0.03 m/s. In one exemplary embodiment, these intervals 116 are excluded until the lid speed has stabilized again. In this case, there is a wait until the speed is less than the limiting value for a predetermined time.

Secondly, a substitute value may be calculated for previously excluded intervals 116.

In one exemplary embodiment, this substitute value is made up of the 90th percentile of eye-opening degree 104 of the last 150 seconds.

In one exemplary embodiment, the last valid value is used in invalid intervals 116. This procedure may be referred to as Sample & Hold.

If invalid intervals 116 are calculated with a smoothed median 114, smoothed median 114 may also be used directly as substitute value.

Thirdly, instantaneous eye-opening level 102 is calculated using substitute value 122 for previously excluded intervals 116.

The final eye-opening level may be ascertained with a further filtering of the signal. In one exemplary embodiment, a Savitzky-Golay filter is used for this purpose. Another possibility is to use a further moving median filter.

Figure 2:
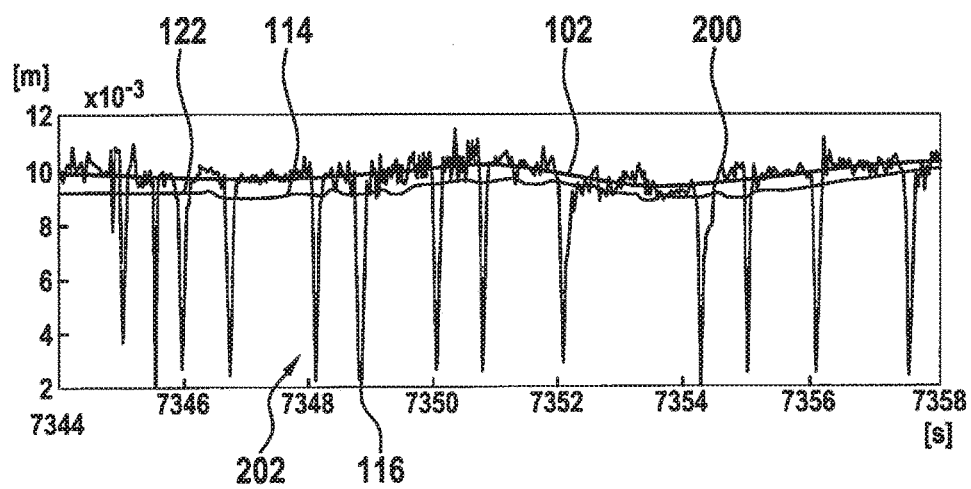
FIG. 2 shows a representation of a characteristic of an eye-opening width and a reference level according to one exemplary embodiment.

FIG. 2 shows a representation of a characteristic 200 of an eye-opening width and a reference level 102 according to one exemplary embodiment. Characteristic 200 is plotted in a diagram that has a time plotted in seconds (s) on the abscissa and a distance plotted in millimeters (m×10$^{-3}$) on the ordinate. For instance, characteristic 200 corresponds to a section of an eye-opening-width signal, as in FIG. 1. Reference level 102 has been ascertained by a method according to the approach presented here. Values 200 of the eye-opening width fluctuate predominantly around the ten millimeters. During a blink 202, the eye-opening width drops briefly toward zero. By the approach presented here, values 116 of the eye-opening width during blink 202 are not utilized for the calculation of reference level 102.

To that end, the values of characteristic 200 are compared to a limiting value 114 which is lower by a few millimeters than current reference level 102. Below limiting value 114, a blink 202 is recognized and values 116 are not used for calculating reference level 102.

To permit the use of an uninterrupted characteristic for calculating reference level 102, the positions in characteristic 200 are filled with support values 122. Support values 122 correspond here to limiting value 114. Therefore, reference level 102 is not lowered by blinking 202.

Figure 3:
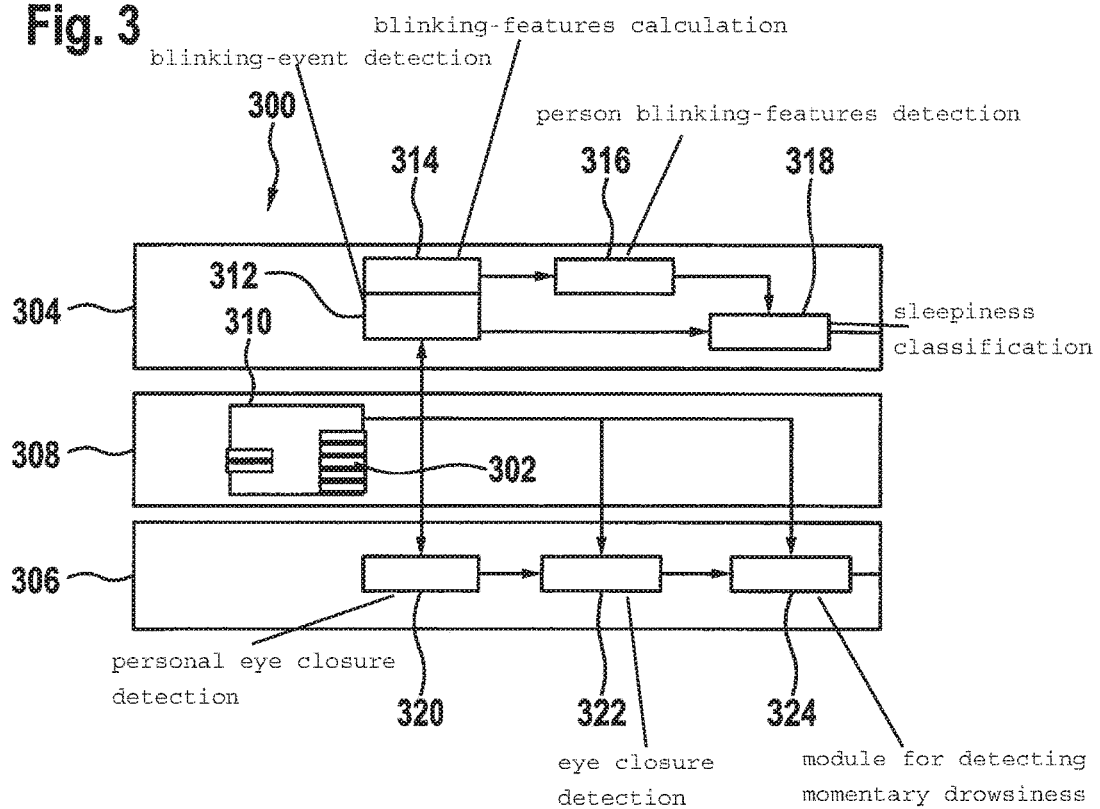
FIG. 3 show a representation of an architecture of an overall system for monitoring the drowsiness of a driver of a vehicle according to one exemplary embodiment.

FIG. 3 shows a representation of an architecture of an overall system 300 for monitoring the sleepiness of a driver of a vehicle according to one exemplary embodiment. Provision 302 of a reference level introduced here is part of system 300 shown here.

Overall system 300 has three main components 304, 306, 308. First main component 304 is denoted as sleepiness classification. Second main component 306 is referred to as momentary-drowsiness detection. Third main component 308 includes modules 310 used jointly by sleepiness classification 304 and momentary-drowsiness detection 306. Provision 302 of the reference level is part of third main component 308. Modules 310 may be referred to as eye-closure preprocessing 310. Eye-closure preprocessing 310 includes sensing of the eye closure on the right side and on the left side, filtering of the eye closure, detecting the speed of the eye closure, an acc of the eye closure, provision 302 of the reference level and a validation.

Eye-closure preprocessing 310 outputs an instantaneous eye closure, an eye-closure speed and the reference level.

In sleepiness classification 304, these values are used in a blinking-event detection 312, and blinking events are passed on to a blinking-features calculation 314.

Blinking-features calculation 314 outputs blinking features to a personal blinking-features detection 316 and a module 318 for the sleepiness classification. The module reads in a personal blinking behavior from blinking-features detection 316 and outputs a sleepiness level.

In momentary-drowsiness detection 306, the values are used in a personal eye-closure detection 320, an eye-closure detection 322 and a module 324 for detecting momentary drowsiness.

Personal eye-closure detection 320 outputs a personal open-eye level and a personal closed-eye level. Both are used by eye-closure detection 322 to provide a binary eye-open value for module 324. Module 324 outputs momentary-drowsiness events.

Sleepiness and momentary drowsiness at the wheel can lead to dangerous situations or accidents. Therefore, a warning may be output when the driver exceeds a certain sleepiness limiting value. For example, a coffee cup may be faded in. This warning may also be ignored by the driver.

To recognize blinking events from an eye-opening signal, what is referred to as a reference amplitude may be used for "normal" blinking events. In this context, "normal" blinking events may be identified by a duration of the closing phase and the plateau phase. The amplitudes for these "normal" blinking events are accumulated. The 85th percentile of these amplitudes may be used as reference amplitude.

With the aid of this reference amplitude, blinking events are able to be differentiated from other eye-movement events with an amplitude <70% of the reference amplitude as well as intentional closing movements with an amplitude >150% of the reference amplitude.

The maximum and minimum eye-opening values may be calibrated robustly. In so doing, all intervals are accumulated in which the speed of the eyelid is zero. Of all these accumulated values, in each case the 10th and 90th percentile are regarded as personal and instantaneous maximum and minimum, respectively. This is a function not only of physiological conditions of the driver, but also of situational conditions such as the current lighting situation, for example.

Preprocessing steps for increasing the detection quality of the eye-opening signal may be carried out in the course of an eye-closure preprocessing (ECP). At the same time, a momentary-drowsiness detection may be integrated. The eye-opening level may also take place in the context of the eye-closure preprocessing. The eye-opening level may subsequently be used within the context of a blink-event detection (BED) and a blink-feature calculation (BFC).

Figure 4:
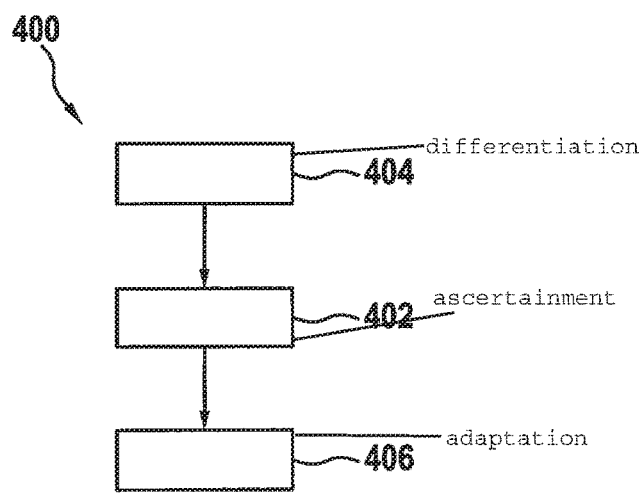
FIG. 4 shows a flowchart of a method for providing a reference level for an eye-opening width according to one exemplary embodiment.

FIG. 4 shows a flowchart of a method 400 for providing a reference level for an eye-opening width according to one exemplary embodiment. Method 400 has an ascertainment step 402. For example, method 400 may be carried out using an apparatus as illustrated in FIG. 1. In ascertainment step 402, the reference level is ascertained using values of the eye-opening width, where the eye-opening width is greater than a limiting value. Ascertainment step 402 is preceded by a differentiation step 404. In differentiation step 404, the values of the eye-opening width are differentiated into values above the limiting value and values below the limiting value.

In one exemplary embodiment, ascertainment step 402 is followed by an adaptation step 406. In adaptation step 406, the limiting value is altered using the reference level.

If an exemplary embodiment includes an "and/or" link between a first feature and a second feature, this is to be read in such a way that the exemplary embodiment according to one specific embodiment has both the first feature and the second feature, and according to a further specific embodiment, has either only the first feature or only the second feature.

What is claimed is:

1. A system for monitoring a sleepiness level of a driver of a vehicle based on a reference level for an eye-opening width, the eye-opening width representing an instantaneously detected distance between the eyelids of an eye, the system comprising:
    a sensing system in the vehicle which senses, at least one eye of the driver of the vehicle, the sensing system including a video camera; and
    an electrical unit configured to ascertain a reference level for an eye-opening width, wherein the apparatus ascertains the reference level by obtaining values of the eye-opening width over a predetermined period of time based on data from the video camera, comparing the obtained values to a limiting value, and determining the reference level using only those of the values that are greater than the limiting value, wherein the limiting value is a moving median of the values of the eye-opening width, the moving median having a window length of at least double a maximum blink duration;
    the electrical unit further configured to:
        ascertain an instantaneous eye closure;
        ascertain an eye closure speed;
        determine a sleepiness level based on the ascertained reference level, ascertained instantaneous eye closure, and ascertained eye closure speed; and
        output, via a display device in the vehicle, a warning signal to the driver based on the determined sleepiness level.

2. A non-transitory machine-readable storage medium storing a computer program for monitoring a sleepiness level of a driver of a vehicle based on a reference level for an eye-opening width, the eye-opening width representing an instantaneously detected distance between the eyelids of an eye, the computer program, when executed by a processor, causing the processor to perform:
    sensing, via a sensing system in the vehicle, at least one eye of the driver of the vehicle, the sensing system including a video camera;
    ascertaining a reference level for an eye-opening width, the ascertaining of the reference level including obtaining values of the eye-opening width over a predetermined period of time based on data from the video camera, comparing the obtained values to a limiting value, and determining the reference level using only those of the values that are greater than the limiting value, wherein the limiting value is a moving median of the values of the eye-opening width, the moving median having a window length of at least double a maximum blink duration;
    ascertaining an instantaneous eye closure;
    ascertaining an eye closure speed;
    determining a sleepiness level based on the ascertained reference level, ascertained instantaneous eye closure, and ascertained eye closure speed; and
    outputting, via a display device in the vehicle, a warning signal to the driver based on the determined sleepiness level.

3. A method for monitoring a sleepiness of a driver of a vehicle, the method comprising:
    sensing, via a sensing system in the vehicle, at least one eye of the driver of the vehicle, the sensing system including a video camera;
    ascertaining a reference level for an eye-opening width, the eye-opening width representing an instantaneously detected distance between the eyelids of an eye of the driver, the ascertaining of the reference level including obtaining, based on data from the video camera, values of the eye-opening width over a predetermined period of time, comparing the obtained values to a limiting value, and determining the reference level using only those of the values that are greater than the limiting value, wherein the limiting value is a moving median of the values of the eye-opening width, the moving median having a window length of at least double a maximum blink duration;
    ascertaining an instantaneous eye closure;
    ascertaining an eye closure speed;
    determining a sleepiness level based on the ascertained reference level, ascertained instantaneous eye closure, and ascertained eye closure speed; and
    outputting, via a display device in the vehicle, a warning signal to the driver based on the determined sleepiness level.

4. The method as recited in claim 3, wherein, in the ascertaining step, the reference level is also ascertained using support values, the support values replacing those values of the eye-opening width which are less than the limiting value.

5. The method as recited in claim 3, further comprising: adapting the limiting value using the reference level.

6. The method as recited in claim 5, wherein the adapting step includes at least one of tracking and interpolating support values which replace values of the eye-opening width that are less than the limiting value.

7. The method as recited in claim 3, wherein in the ascertaining step, the reference level is also ascertained using a speed limiting value, the values of the eye-opening width being used when an eyelid speed is less than the speed limiting value.

8. The method as recited in claim 3, wherein in the ascertaining step, ascertaining the reference level as reference characteristic, a time characteristic of the eye-opening width being used in intervals in which the values of the eye-opening width are greater than the limiting value.

9. The method as recited in claim 8, wherein in the ascertaining step, the values of the eye-opening width are smoothed.

10. The method as recited in claim 3, wherein the window length is two seconds.

11. The method as recited in claim 3, wherein outputting of the warning signal includes outputting a visual image to the driver.

12. The method as recited in claim 11, wherein the visual image is an imaging of a coffee cup.

13. The method as recited in claim 3, wherein the window length is two seconds.

14. A method for monitoring a sleepiness level of a driver of a vehicle based on a reference level for an eye-opening width, the eye-opening width representing an instantaneously detected distance between the eyelids of an eye, the method comprising:

sensing, via a sensing system in the vehicle, at least one eye of the driver of the vehicle, the sensing system including a video camera;

ascertaining a reference level for an eye-opening width using values of the eye-opening width, the ascertaining including obtaining eye-opening widths and speeds of the eyelids over time based on data from the video camera, comparing the obtained speeds of the eyelids to a speed limiting value, and averaging the obtained eye-opening widths over time to ascertain the reference level, wherein only those eye-opening widths obtained during a time interval in which the speed of the eyelids are less than the speed limiting value are used in the averaging;

ascertaining an instantaneous eye closure;

ascertaining an eye closure speed;

determining a sleepiness level based on the ascertained reference level, ascertained instantaneous eye closure, and ascertained eye closure speed; and outputting, via a display device in the vehicle, a warning signal to the driver based on the determined sleepiness level.

15. A method for monitoring a sleepiness level of a driver of a vehicle based on a reference level for an eye-opening width, the eye-opening width representing an instantaneously detected distance between the eyelids of an eye, the method comprising:

sensing, via a sensing system in the vehicle, at least one eye of the driver of the vehicle, the sensing system including a video camera;

ascertaining a reference level for an eye-opening width using values of the eye-opening width, the ascertaining including determining a time characteristic of eye-opening widths based on data from the video camera, comparing values of the time characteristic to a limiting value, and averaging only those values of the time characteristic which are greater than the limiting value to ascertain the reference level, wherein the limiting value is a value that is lower than a current reference level;

ascertaining an instantaneous eye closure;

ascertaining an eye closure speed;

determining a sleepiness level based on the ascertained reference level, ascertained instantaneous eye closure, and ascertained eye closure speed; and outputting, via a display device in the vehicle, a warning signal to the driver based on the determined sleepiness level.

\* \* \* \* \*